(12) United States Patent
Chang

(10) Patent No.: US 6,257,884 B1
(45) Date of Patent: Jul. 10, 2001

(54) MAXILLOMANDIBULAR FIXATION DEVICE

(76) Inventor: Peter Chang, 14702 Forest Wood La., Midlothian, VA (US) 23112

( * ) Notice: Subject to any disclaimer, the term of this patent is extended or adjusted under 35 U.S.C. 154(b) by 0 days.

(21) Appl. No.: 09/418,363

(22) Filed: Oct. 14, 1999

(51) Int. Cl.$^7$ .................................................. A61C 5/00
(52) U.S. Cl. ............................................. 433/18; 433/215
(58) Field of Search ................................. 433/18, 19, 20, 433/215

(56) References Cited

U.S. PATENT DOCUMENTS

| | | |
|---|---|---|
| 274,367 | 3/1883 | Patrick . |
| 1,797,481 | 3/1931 | Preston . |
| 2,481,177 | 9/1949 | Tofflemire . |
| 2,502,902 | 4/1950 | Tofflemire . |
| 3,348,311 | * 10/1967 | Weissman . |
| 3,526,961 | 9/1970 | Kesling . |
| 3,913,228 | 10/1975 | Wallshein . |
| 4,090,299 | 5/1978 | Williams . |
| 4,202,328 | 5/1980 | Sukkarie . |
| 4,230,104 | 10/1980 | Richter . |
| 4,292,025 | 9/1981 | Forster . |
| 4,318,694 | * 3/1982 | Klein ........................................ 433/22 |
| 4,384,854 | * 5/1983 | Garfinkel ............................. 433/215 |
| 4,813,869 | 3/1989 | Gatewood . |
| 4,872,449 | 10/1989 | Beeuwkes, III . |
| 4,968,248 | * 11/1990 | McColgan et al. ...................... 433/18 |
| 5,328,364 | * 7/1994 | Doyle ...................................... 433/18 |
| 5,842,856 | 12/1998 | Casey . |
| 6,086,365 | * 7/2000 | Fields ...................................... 433/18 |

FOREIGN PATENT DOCUMENTS

| | | |
|---|---|---|
| 601835 | 8/1934 | (DE) . |
| 831743 | * 2/1952 | (DE) ...................................... 433/18 |

OTHER PUBLICATIONS

R. Hopkins—*Mandibular fractures: treatment by closed reduction and indirect skeletal fixation* (no date).

* cited by examiner

*Primary Examiner*—Ralph A. Lewis
(74) *Attorney, Agent, or Firm*—Pitts & Brittian, P.C.

(57) ABSTRACT

A maxillomandibular fixation apparatus for locking teeth of the lower jaw and/or teeth of the upper jaw together to allow a fractured maxilla or mandible to heal. The apparatus includes a flexible arcuate arch bar that is positionable on the interior side of the teeth of a fractured jaw. A plurality of flexible receptacle segments are anchored onto the interior arch bar and include arms positioned to project from the arch bar between the teeth of the upper or lower jaws. Each segment arm includes a distal end that extends outward from each side of respective teeth towards the patient's cheeks. A separate exterior receiving bar can be aligned around the exterior surfaces of the teeth, the exterior receiving bar having holes therethrough for insertion of the distal ends of the segment arms. A plurality of lug nuts can be fastenable to the distal ends, clamping the exterior receiving bar against the exterior side of the teeth, and drawing tight the interior arch bar against the inside of the teeth. During wear, the lug nuts can be adjusted to change the distance between exterior and interior arch bars. The exterior lug nuts form an junction exterior to the teeth onto which ligature wire or elastic bands can be connected between upper and lower exterior receiving bars attached to upper and lower interior arch bars, to fixate the mandible and maxilla teeth and jaws together for healing.

20 Claims, 4 Drawing Sheets

MAXILLOMANDIBULAR FIXATION DEVICE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to a device for fixation of a fractured jaw, and more specifically to a fixation device for locking the teeth of the upper and/or lower jaw for therapeutic purposes.

2. Description of the Related Art

Medical treatises advise that mandibular simple and compound fractures can be treated by closed reduction and indirect skeletal fixation of the lower or upper jaw. Prior devices have been utilized for locking the teeth of the lower jaw (the mandible) together, for locking the teeth of the upper jaw (the maxilla) together, and for locking the upper and lower jaws together to allow a broken maxilla or mandible to heal after a fracture. The prior devices utilized a multitude of wires, plates, connectors, arch bars, and screws that are cumbersome and time consuming to install in the moist and limited space of a patient's mouth. One of the multitude of pieces utilized to fixate the jaws and teeth could easily be left unattached in the patient's mouth and potentially swallowed by the patient. In addition, the prior devices typically required an extensive time for installation within the patient's mouth, requiring general anesthesia for the patient during installation.

Typical of the prior art are those jaw fixation devices disclosed in the following U.S. Patents. In U.S. Pat. No. 5,842,856, to Casey, a release system for treatment of a broken jaw is disclosed that includes an upper and lower arch bar that is attachable on the outer sides of the teeth. A release bar is insertable through a plurality of loops extending downward from the upper arch bar, with a similar release bar extending upwards from the lower arch bar, allowing wires to be threaded between loops of the upper release bar and loops of the lower release bar to secure the outer sides of teeth of the upper jaw to the outer sides of teeth of the lower jaw. The plurality of loops of each release bar are attached to hangers that must be secured to the exterior sides of the teeth by wrapping ligature wire around the teeth at the gum level and threading the wire through the hangers. The use of ligature wire presents the opportunity of breakage of wires, the risk of puncture of tissue within the mouth, and the need for re-wrapping of each release bar and associated hangers with ligature wire during replacement of broken wires of either upper or lower arch bars. The release bars and hangers are not used on the interior of teeth.

In U.S. Pat. No. 4,872,449, to Beeuwkes, a quick-release device for maxillomandibular stabilization is disclosed that includes a plurality of splints or units of interfitting connector plates. The plates are interconnected with archwire passing through interfitting slots in each connector plate. Each connector plate is connected to the outside exterior of adjacent teeth by U-shaped anchor members such as wires that encircle the teeth and have threaded extremities that pass through holes in the connector plates. Retainer elements such as screws or retainer nuts are screwed onto the threaded extremities for holding the connector plates tightly against the outside exterior of adjacent teeth. The interfitting connector plates form a set including one plate for one or two lower teeth and a separate plate for one or two upper teeth, are interconnected with the archwire, which serves as an exterior or buccal retainer bar. The retainer elements are screwed onto the exterior or buccal side of the teeth. Each unit of connector plates that locks an upper and lower tooth together can include approximately eight pieces that must be removed before a segment of upper and lower teeth are freed from containment, thereby requiring use of, and removal of, a plurality of small items from the mouth of the patient before the patient's jaw is movable. The plurality of small items are cumbersome to install in the moist confines of a patient's mouth and requires scrutiny to minimize loss of connector plates, retainer elements, and/or anchor members within the patient's mouth.

In U.S. Pat. No. 4,813,869, to Gatewood, a jaw fixation assembly is disclosed that includes anchor members that encircle each tooth. Each anchor member includes bendable wires that form around the lingual surfaces of each tooth, with the ends of the wires extending on the buccal side of each tooth, and each wire end secured by retainer members that are screwed onto the wire ends projecting between the teeth. A metal band can be attached between the buccal ends of the wires projecting between the teeth, with the retainer members screwed onto the wire ends extending on the exterior side of each tooth. A plurality of ligature wires can be attached between the retainer members located on the exterior or buccal sides of the maxillary teeth, to the retainer members located on the exterior or buccal sides of the mandibular teeth. The jaw fixation assembly requires at least four parts for fixation of each tooth, with no common arch bar established around the exterior, or within the interior side of the teeth. A plurality of ligature wires is required to secure the maxillary teeth to the mandibular teeth. A special elongated tool is required for tightening each anchor member on the ends of each bendable wire encircling the teeth.

In U.S. Pat. No. 4,230,104, to Richter, an orthodontic appliance is disclosed that comprises a malleable upper and lower arch bar having exterior ligature wire that are adaptable around the individual teeth to hold the teeth, with a prong and tab projecting from the exterior surface of the arch bars. The prong and tab structure provides attachment points for ligature wires that can be wrapped between the upper and lower arch bars. The appliance only provides an arch bar on the exterior of the teeth, and is not easily removable due to the multiple prongs, tabs, and ligature wires that must be loosened and removed from the upper and lower arch bars to separate the patient's jaws.

U.S. Pat. No. 2,481,177, to Tofflemire, discloses an appliance for holding undamaged teeth together while a fractured jawbone heals, the appliance comprises individual abutments or fixation blocks that are secured to anchor teeth, with wire staples passing around the anchor teeth and through bores in the abutments to secure the anchor teeth to the abutments. Wire interconnections between upper and lower abutments and alignment bars are installed and removed with special cutting, pulling, and crimping tools.

Therefore, it is an object of the present invention to provide an apparatus for fixation of some or all of the teeth of the upper jaw together.

It is another object of the present invention to provide an apparatus for fixation of the some or all of the teeth of the lower jaw together.

It is another object of the present invention to provide an apparatus for fixation of teeth of the upper jaw and the teeth of the lower jaw, along with fixation of the upper and lower jaws together.

It is another object of the present invention to provide an apparatus for expedited installation under local anesthesia of maxillomandibular fixation arch bars to lock teeth to be fixated of the upper and lower jaws together.

BRIEF SUMMARY OF INVENTION

In accordance with the present invention, there is provided an apparatus for locking teeth together of the lower jaw, for locking the teeth of the upper jaw together, and/or for locking the upper and lower jaws together to allow a broken maxilla, mandible, or dentoalveolar apparatus to heal after a fracture. The maxillomandibular fixation apparatus includes a plurality of individual U-shaped female receptacle segments that can fit between teeth of the mandible and maxilla, with each female receptacle segment anchored on the lingual side of the tooth to an interior arch bar. Adjacent receptacle segments will include a base portion of the lingual arch bar with exposed arms extending outwards from the arch bar in a U-shape, extending between teeth to be fixated and towards the cheeks and lips of the patient. The lingual arch bar and adjacent receptacle segments allow encircling of the teeth from the lingual, medial, and distal aspects, leaving the buccal aspect open.

A first, interior arch bar is aligned inside the interior, or lingual surfaces of the mandible and/or maxilla teeth, in a configuration adjacent to, and extending along the interior surfaces of the teeth. The interior arch bar includes a plurality of individual, tubular U-shaped female receptacle segments that are permanently or temporarily connectable at the base of each segment to the interior arch bar, which is secured to the teeth by the exposed arms of each segment which extend between the teeth at the gum level, or base, of each tooth. An arcuate and malleable receiving bar having a plurality of holes can be aligned around the exterior, or buccal surfaces of the mandible and/or maxilla teeth. The receiving bar can be secured to the interior arch bar by insertion of the distal ends of each arm of each segment through holes in the receiving bar. The patient's teeth can be locked together between the bars after insertion of each distal end of each receptacle segment through the holes in the exterior receiving bar by fastening a lug nut to each distal end of each segment, therefore drawing tight the interior arch bar, and exterior malleable receiving bar against the teeth of the mandible and/or maxilla. Each individual U-shaped receptacle segment can be sized in length for average sized teeth and can be cut to size for any individual's teeth.

Each lug nut connects a certain distance into, or onto, the respective distal end of each female segment with the connection length dependent on the fixation requirements for the teeth to be fixated, and the jaw(s) to be fixated. During wear, the lug nuts can be tightened into the buccal interproximal sides of teeth, or loosened outwards, to bring the interior arch bar, and exterior receiving bar closer, or further, apart as most oral fixation devices tend to loosen under normal use. The exterior or buccal side of each lug nut that protrudes from the distal ends of each arm of each female segment can be interconnected to other lug nuts by ligature wire and/or elastic bands, to connect the mandible teeth and the maxilla teeth together for jaw fixation.

BRIEF DESCRIPTION OF SEVERAL VIEWS OF THE DRAWINGS

The above mentioned objects and advantages of the present invention are readily apparent from description of the invention contained herein, and by reference to the claims, read together with the drawings in which:

DETAILED DESCRIPTION OF THE INVENTION

Figure 1:
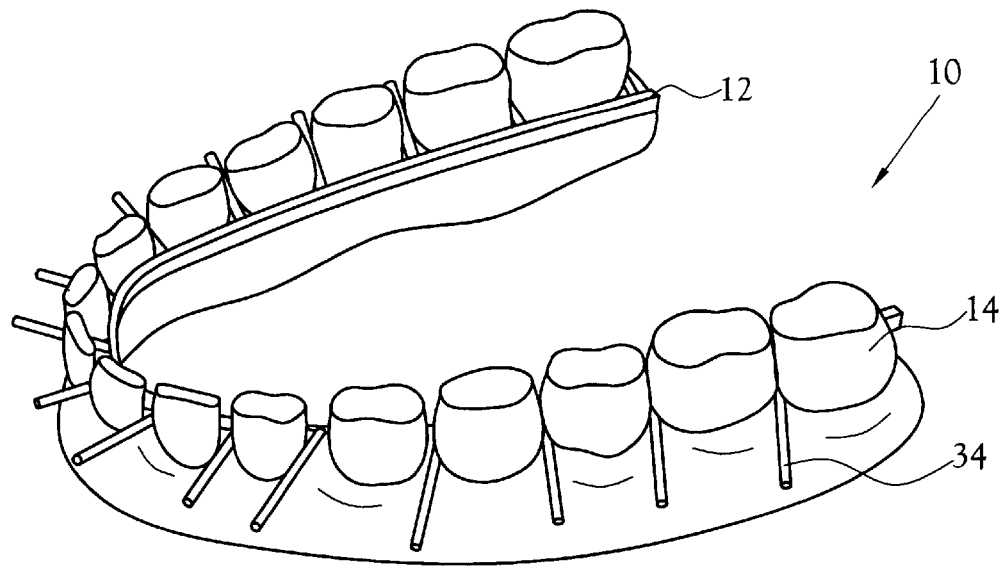
FIG. 1 is a perspective view of one embodiment of an apparatus for maxillomandibular fixation of the present invention.

In accordance with the present invention, there is provided a maxillomandibular fixation device 10 for fixation of the upper and lower jaw of a patient for therapeutic purposes, incorporating various features illustrated generally in the FIGS. 1–9. In the following description, the term maxilla-, refers to the upper jaw, and associated teeth, and the term mandibula, refers to the lower jaw, and associated teeth.

The maxillomandibular fixation device 10 is utilized for locking the mandibular teeth of the lower jaw together, for locking the maxillary teeth of the upper jaw together, and/or for locking the upper and lower jaws together to allow a broken maxilla, mandibular, and/or dentoalveolar apparatus to heal after a fracture. A first, interior arch bar 12 is aligned inside the interior, or lingual surfaces of the mandibular 14 and/or maxillary 16 teeth, in a configuration adjacent to and extending along the interior surfaces of the teeth. The maxillomandibular fixation device 10 can also include a second, interior arch bar 22 (not shown in FIG. 8), that is aligned inside the lingual surfaces of the teeth of the jaw opposite the placement of the first, interior arch bar 12. The interior arch bar 12 has a generally elongated cross-section with generally planar internal and external side surfaces, with a U-shaped curvature of the arch bars (see FIGS. 1, 2 and 7). The arch bar includes interior facing surface 18 (24 for second arch bar, not shown), and exterior facing surface 20 (26 for second arch bar, not shown). The interior arch bars are pliable and can be composed of stainless steel, preferably of twenty to twenty-four gauge stainless steel, or of a material having a similar gauge and strength that can be adjust to the curvature of the oral cavity and that does not degrade when left in the oral cavity for extended periods.

Figure 2:
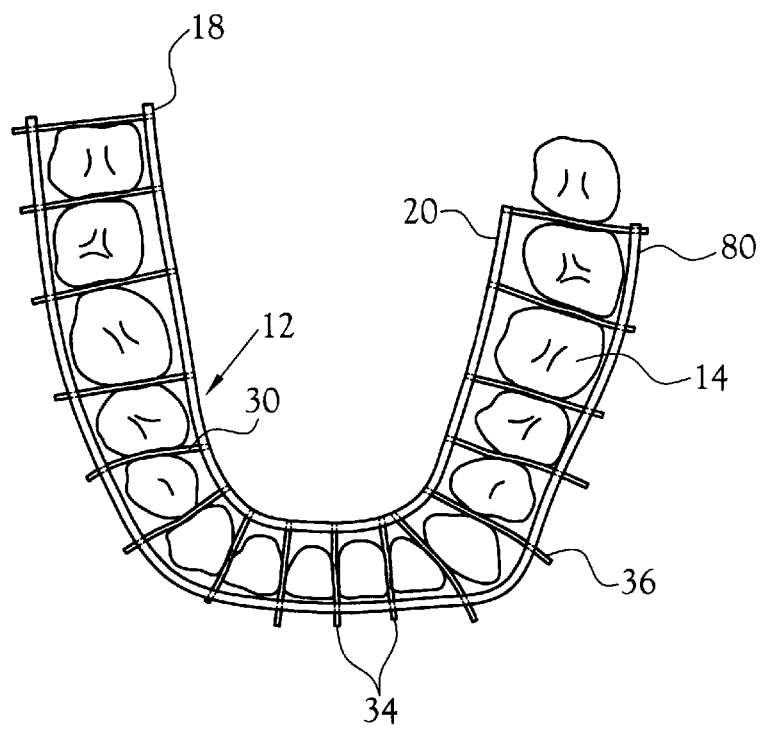
FIG. 2 is a top view of the interior arch bar and exterior receiving bar installed in a patient's mouth.
Figure 4:
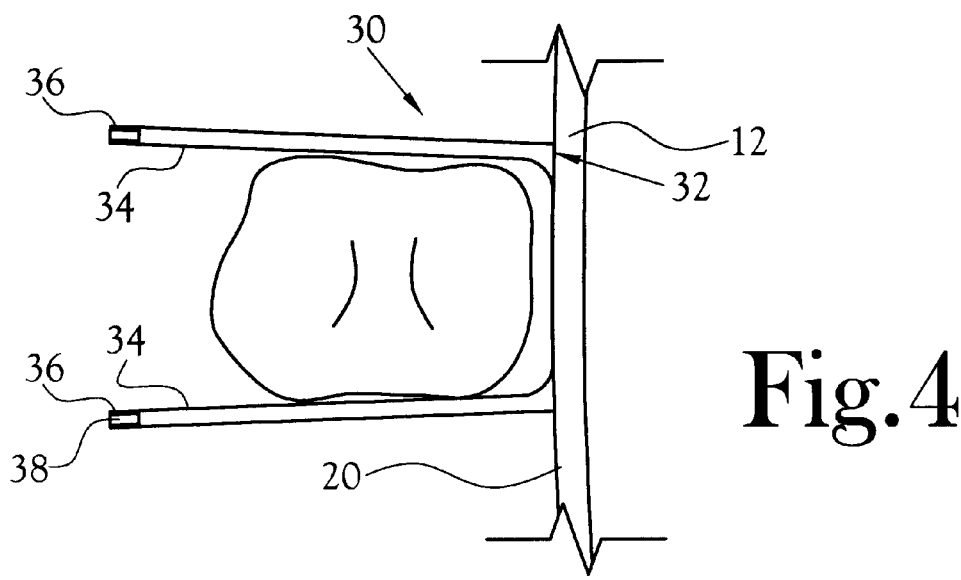
FIG. 4 is a top view of a U-shaped receptacle segment encircling a tooth.
Figure 5:
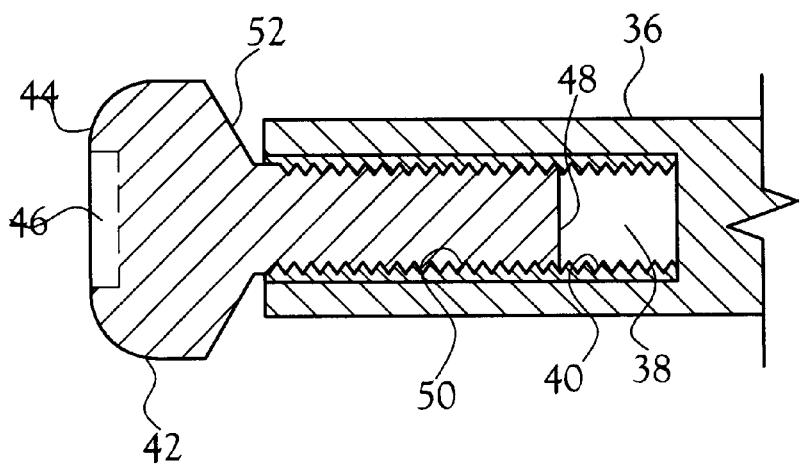
FIG. 5 is a partial cutaway view of one end of an arm of the receptacle segment of FIG. 4, illustrating lug nut connections and the length of the thread interior of an arm.
Figure 6:
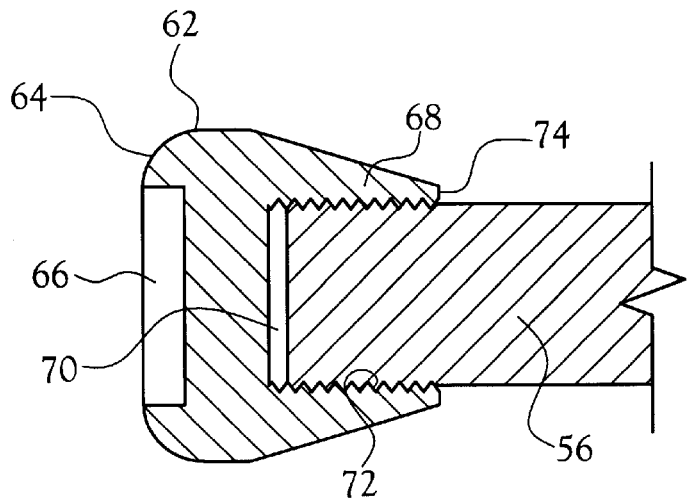
FIG. 6 is an exploded view of FIG. 4, illustrating an alternative configuration of the lug nuts connecting to one end of an arm of the receptacle segment.

The interior arch bar 12 includes a plurality of individual U-shaped receptacle segments 30 that are connectable at the lingual base 32 end of each segment 30 to the exterior facing surface 20 of the interior arch bar 12 (see FIGS. 2 and 4). An alternative embodiment provides for the lingual base 32 end of each segment 30 to connect into the interior arch bar. Each receptacle segment 30 includes a cylindrical or oval cross-section, with each segment having extending arms 34 that project in the same general direction outward from the lingual base 32 of each segment 30. The arms are pliable and can be composed of stainless steel, preferably of twenty to twenty-two gauge stainless steel, or of a similar metal that does not degrade when left in the mouth of a patient for months.

The pliable arms extend outward from the exterior facing surface 20 of the interior arch bar 12 (second interior bar 22, not shown). Each adjacent pair of arms 34 can encircle one tooth of the mandible or maxilla, with a plurality of pairs of arms 34 aligned side-by-side. The plurality of arms 34 are each connected to the interior arch bar 12 (second interior arch bar 22, not shown), at the lingual base 32 of each pair of arms, the base being anchored on the lingual side of the tooth to the interior arch bar 12 (22, not shown). Each lingual base 32 can be soldered onto, connected into, or otherwise bonded to the interior arch bar 12.

The distal end 36 of each pair of arms 34 can be formed as a female receptacle arrangement having a cylindrical cross-section and a hollow threaded interior such as a blind internal bore 38, with the internal bore including a depth into the distal end 36 of approximately one mm. The internal bore 38 includes interior wall threads 40 that will accept a releasably insertable miniature screw connector or lug nut 42 (see FIG. 5). The lug nut 42 includes a first contoured end 44 having a blind hexagonal bore 46 in the first end 44, and includes an insertion end 48. The insertion end 48 includes exterior threads 50 that, when end 48 is inserted into the internal bore 38 of the distal end 36, the threads 50 of end 48 connect with interior threads 40 of the distal end 36, forming a junction 52 of each lug nut 42 with each distal end 36. When the interior arch bar 12 is positioned inside the maxillary 16 and mandibular 14 teeth, each pair of arms 34 are positionable to extend between teeth to be fixated, projecting through the interproximal gap between adjacent tooth, or between every other or every few teeth at the gum or base level of each tooth. The distal ends 36 project outwards between the interproximal corners of the teeth, towards the exterior, buccal side of the teeth, and towards the cheeks of the patient. The insertion end 48 of each lug nut 42 threads into each internal bore 38 of each distal end 36, providing a secure fit of lug nuts 42 against exterior, buccal (cheek side), interproximal (between teeth) surfaces of the teeth. An excess in length of the threads on each distal end allow adjustments for tightening and loosening to adjust for variability of tooth sizes and interproximal gaps between teeth. The tightening of the lug nuts 42 against the buccal, interproximal surfaces of the teeth secure the interior arch bar 12 (second interior arch bar 22, not shown) against the cervical collar, or cemento-enamel junction of teeth, to fixate teeth in proper position in relation to each other, and in relation to a fractured upper and/or lower jaw.

An alternate configuration for the receptacle segments 30 is each alternate distal end 56 includes a solid, cylindrical end 58, with exterior threads 60 on the external surface of each distal end 56. The alternate lug nuts 62 include a first end 64 having a blind hexagonal bore 66 in the first end 64, and includes a connector end 68, having a hollow interior, or a blind internal bore 70, with the internal bore including a depth into the connector end 68 of approximately ½ mm to approximately one mm. The internal bore 70 can have an interior threaded surface 72 that can thread releasably into the exterior threads 60 of the alternate distal end 56' (see FIG. 6). The internal bore 70 of the connector end 68 of the alternate lug nuts 62 fit over the alternate distal end 56, connecting the exterior threads 60 of the distal end 56, forming a junction 74 of each alternate lug nut 62 with each alternate distal end 56. When the interior arch bar 12 is positioned inside the maxillary 16 and mandibular 14 teeth, each pair of arms 34 are positionable to extend between teeth to be fixated, projecting through the gap between each tooth at the gum level, or base of each tooth, with the alternate distal ends 56 projecting towards the cheeks of the patient. The connector end 68 of each alternate lug nut 62 threads onto the exterior threads 60 of each alternate distal end 56, providing a firm conforming fit of the alternate lug nuts 62 against the exterior surfaces of the teeth, and the interior arch bar 12 (second interior arch bar 22, not shown) conforming against the interior of the teeth, to fixate the teeth in proper position in relation to each other, and in relation to a fractured upper and/or lower jaw.

Figure 3:
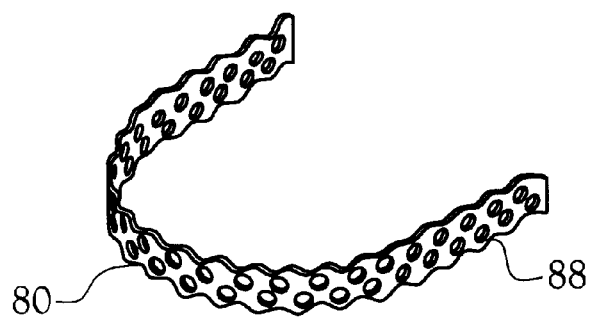
FIG. 3 is a perspective view of the exterior receiving bar.
Figure 7:
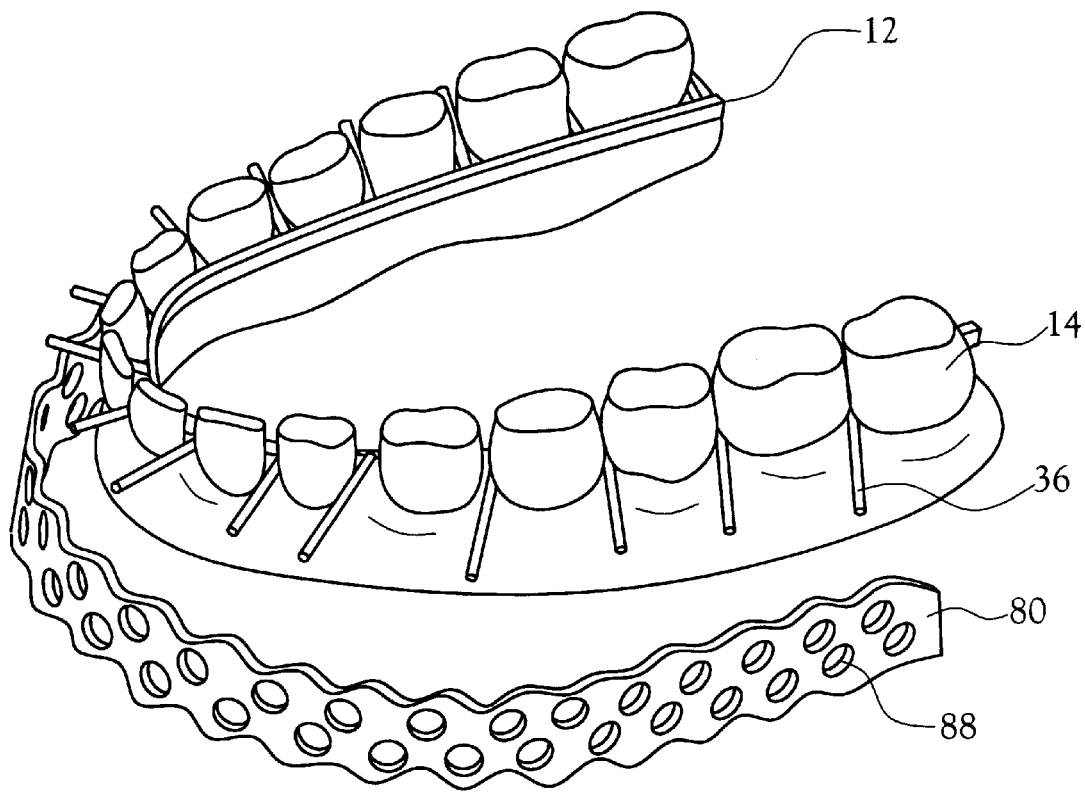
FIG. 7 is a perspective view of the installed interior arch bar and the positioning of the exterior receiving bar.
Figure 8:
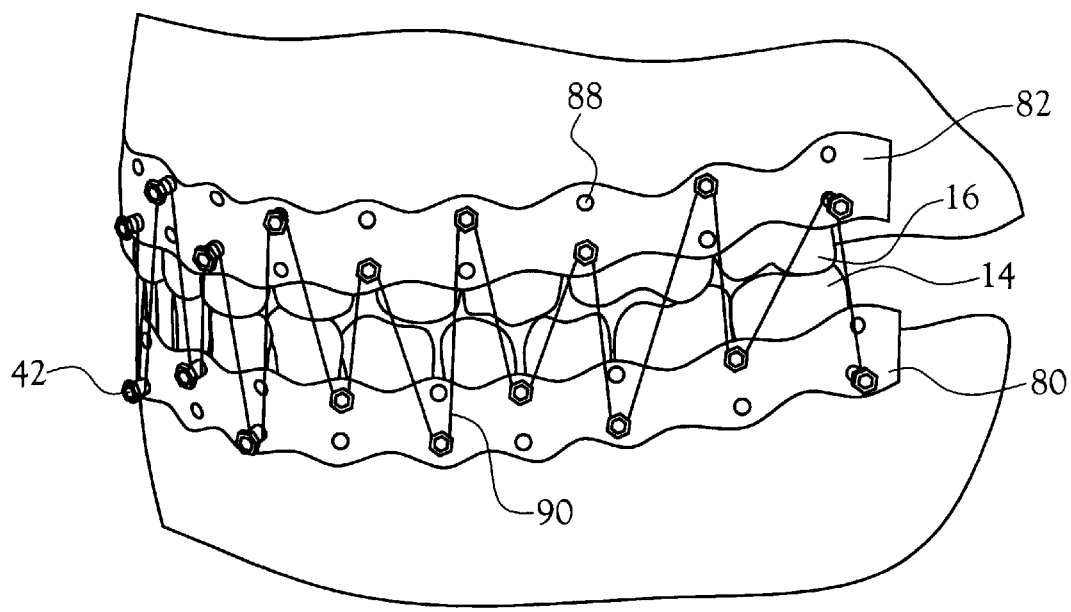
FIG. 8 is a perspective view of two exterior receiving bars connected together with ligature wires.
Figure 9:
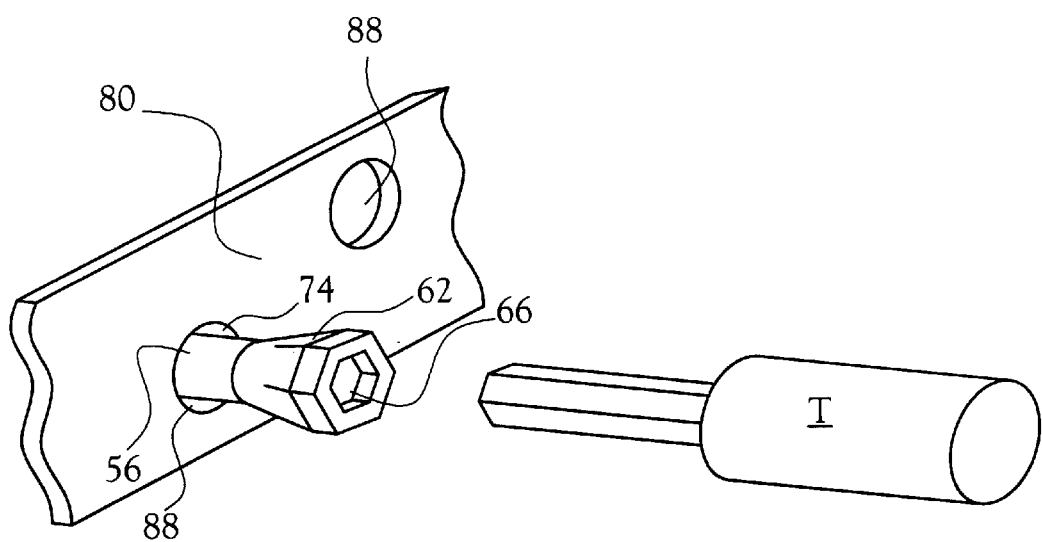
FIG. 9 is a perspective view of the alternate lug nut installed on one end of an arm of the receptacle segment extending through the exterior receiving bar.

The interior arch bar 12 can be implanted interior to either, or both, maxillary and mandibular teeth, and can be utilized with exterior receiving bars 80, 82 (see FIGS. 3, 7, and 8). The exterior receiving bars 80, 82 can be aligned around the exterior, or buccal surfaces of the mandible and/or maxilla teeth, with the exterior receiving bars 80, 82 forming an arcuate, U-shaped, exterior enclosure for teeth to be fixated. The exterior receiving bars 80, 82 can be pliable and composed of stainless steel, or of a material having similar strength as interior arch bar 12. The exterior receiving bars 80, 82 should be flexible to adjust to the curvature of an adult's, or a child's oral cavity, while not degrading when left in the oral cavity for extended periods.

The exterior receiving bars 80, 82 have a generally elongated cross-section with generally planar internal and external side surfaces having edges that are scalloped without sharp edges. A U-shaped curvature allows the exterior receiving bars 80, 82 to match the curvature of the interior arch bar 12. The exterior receiving bars 80, 82 include a plurality of alternating, non-aligned, holes 88 through the planar side surfaces, with the holes capable of accepting the distal ends 36 or 56 of the arms 34 of each receptacle segment 30. Exterior receiving bars 80, 82 can be secured to the interior arch bar 12 by: (a) inserting the interior arch bar 12 on the interior sides of the maxillary and mandibular teeth; (b) positioning each respective pair of arms 34 of the receptacle segments 30 between and around teeth to be fixated; (c) placing the distal ends 36 or 56 on the exterior sides of teeth to be fixated; (d) aligning the exterior receiving bars 80, 82 plurality of holes 88 with the distal ends; (e) inserting the distal ends through the holes so that the distal ends extend through to the exterior side of the exterior receiving bar 80, 82; (f) connecting the appropriate lug nut 42 or 62 into or onto the appropriate distal ends 36 or 56; and (g) tightening the appropriate lug nut 42 or 62 into or onto the appropriate distal ends 36 or 56 with a hexagonal shaped tool T inserted into the first end bore 46 or 66 of each lug nut 42 or 62, to assure a tight, temporary fixation and locking together of the maxillomandibular teeth of a patient having a fractured jaw or jaws, or having a dentoalveolar apparatus installed.

Each lug nut 42 or 62 inserts a certain distance into or onto the appropriate distal ends 36 or 56 of each female segment, with the insert distance dependent on the fixation requirements for the teeth and fractured jaws. During wear, the lug nuts can be tightened, or loosened, to bring the interior arch bar and exterior receiving bar closer, or further apart, adapting the malleable metal or other material components around the interior or exterior sides of each tooth. Each lug nut that projects outwards from the maxillary and/or mandibular teeth can be interconnected to other lug nuts, specifically the exterior junction 52, 74 of each lug nut, by wrapping of metal or high-strength, non-metallic ligature wire 90 and/or elastic bands (not shown), between junctions of lug nuts and distal ends, to wire the mandible teeth and the maxilla teeth together for jaw fixation.

From the foregoing description, advantages will be recognized by those skilled in the art for the apparatus for the maxillomandibular fixation apparatus, including the advantage that the interior arch bar 12 with attached receptacle segments can be insertable as a single unit into a patient's mouth in an upper, maxilla, and/or lower, mandible position with a minimal sequence of manipulations. The single unit of the arch bar 12 can allow for swift emplacement of the arms of the receptacle segments 30 between teeth of the upper and/or lower jaws. Upon positioning of the arch bar 12 interior of the teeth to be fixated, each arm of each segment can be extended between the appropriate interproximal sides of the teeth and appropriate lug nuts attached to the distal ends of the arms, to lock the teeth together with a minimum of motion and time.

The limited number of loose pieces of equipment required by the interior arch bar and exterior receiving bar, with a limited number of attaching lug nuts, allows for locking of the interior arch bar and exterior receiving bars with efficient use of a medical practitioner's time in potentially life-threatening emergency room situations. An additional step provides an exterior receiving bar is positioned around the buccal side of the upper and/or lower teeth, with the arms of each segment extending through the plurality of holes of the exterior receiving bar for lug nuts securing of the exterior receiving bar in rigid orientation with the interior arch bar.

The interior arch bar 12 and exterior receiving bar 80 can be cut and down-sized in length to fit within the oral cavity of a child, or to provide an expedient method of fixation of two or three adjacent teeth, or to fixate two teeth spaced apart from two or more teeth by a missing child's tooth, allowing the gap to be maintained while the child's teeth or jaws heal. In addition, the arch bar 12 can be cut and placed on opposing, interior, lingual sides of the maxilla, and/or mandible teeth, with an associated placement and attachment of an exterior receiving bar 80, either full length or partial length, to fixate teeth on opposing sides of the mouth. The upper and lower jaws can be locked together to assist healing, by wrapping ligature wire 90, and/or elastic bands (not shown), between the lug nuts for fixation of the patient's jaws. A minimum number of parts is utilized and the tension of each lug nut and distal end can be readjusted individually and frequently, on the upper or lower jaws during wear of the fixation device. Expedited installation under local anesthesia is possible for the interior arch bar and exterior receiving bar to quickly lock damaged teeth and fractured jaws together. The interior arch bar and exterior receiving bar can be easily removed together, or the interior arch bars can be left in place with a plurality of lug nuts attached to the distal ends of the receptacle segments arms, without the exterior receiving bar for continued therapy. The use of the exterior receiving bar is optional and dependent on the patient's type of injury. The exterior receiving bar, either in full-arch length, or in partial-half length, can fixate isolated dental injury within the maxilla or within the mandible arch. The exterior receiving bar, can also be sectioned and utilized in segments to stabilize loose teeth on one and/or another side of the patient's mouth, when connected to appropriately sized maxillomandibular interior arch bars teeth.

The internal arch bar can be cut or sectioned for placement in the mandible and/or maxilla, with associated receptacle segments and lug nuts, for therapeutic treatment of as few as two teeth, or any number of teeth that are injured and require fixation. The internal arch bar, with or without the exterior receiving bar, in full U-shaped configuration or sectioned to lesser lengths, can be utilized for any dental disease that causes teeth to be loose and thus requiring immediate temporary or permanent fixation. The internal arch bar, with or without the exterior receiving bar, can be utilized where there is no tooth or gum disease or injury, but maxillomandibular fixation is required during oral surgery.

While a preferred embodiment is shown and described, it will be understood that it is not intended to limit the disclosure, but rather it is intended to cover all modifications and alternate apparatus falling within the spirit and the scope of the invention as defined in the appended claims. One skilled in the art will recognize variations and associated alternative embodiments. The foregoing description should not be limited to the description of the embodiment of the invention contained herein.

What is claimed is:

1. A maxillomandibular fixation apparatus for locking together teeth to be fixated either of the upper and /or lower jaws, and/or for locking the upper and lower jaws together for a patient having a need therefor, the fixation apparatus comprising:

an arcuate arch bar positionable interior of teeth to be fixated either of the upper jaw and lower jaw; said arch bar adapted to be disposed adjacent to and extendable along the inside of teeth to be fixated;

a plurality of receptacle segments, each of said segments including:

a base connectable to said arch bar on the lingual interior side of the teeth; and a plurality of arms extendable radially outward from each base of said receptacle segments, said arms being positionable between teeth to be fixated, said arms having distal ends extendable outward on either side of teeth to be fixated, said distal ends extendable towards the patient's cheeks; and a plurality of lug nuts, said lug nuts being connectable to said distal ends of each arm of said receptacle segments.

2. The maxillomandibular fixation apparatus of claim 1, wherein said arch bar and said plurality of arms of said plurality of receptacle segments are flexibly resilient and are of metal composition.

3. The maxillomandibular fixation apparatus of claim 2, wherein said lug nuts are removably connectable to said distal ends, said lug nuts being in contact with the exterior buccal side of the teeth when tightened toward said arch bar positioned on the lingual interior side of the teeth.

4. The maxillomandibular fixation apparatus of claim 3, wherein said receptacle segments are generally U-shaped, said distal ends having a hollow cylindrical cross-section and internally threaded, said distal ends accepting connection of said lug nuts, said base of each segment rigidly connected to said arch bar installed interior of the teeth.

5. The maxillomandibular fixation apparatus of claim 4, wherein said lug nuts comprise a first end having a blind bore therein, said blind bore having a hexagonal cross-section, and an insertion end having exterior threads for removable insertion into said distal ends of said arms of said receptacle segments.

6. The maxillomandibular fixation apparatus of claim 3, wherein said receptacle segments are generally U-shaped, said distal ends having external threads, said distal ends accepting connection of said lug nuts, said base of each segment rigidly connected to said arch bar installed interior of the teeth.

7. The maxillomandibular fixation apparatus of claim 6, wherein said lug nuts comprise a first end having a blind bore therein, said blind bore having a hexagonal cross-section, and a connection end having a cylindrical blind bore therein, said cylindrical blind bore having internal threads for removable connection to each distal end of said arms of said receptacle segments.

8. The maxillomandibular fixation apparatus of claim 2, wherein said arcuate arch bar further comprises at least two arch bars separately positionable interior of the teeth of the upper and lower jaws, each of said arch bars positionable adjacent to and extending along the interior surfaces of the teeth, each of said arch bars including receptacle segments having arms positionable between teeth to be fixated of the upper and lower jaws, said arms having distal ends extending outward past each respective tooth toward the patient's cheeks.

9. The maxillomandibular fixation apparatus of claim 8, wherein said distal ends accept said lug nuts, said lug nuts form a junction with each arm, said junction accepts ligature wire and/or elastic bands wrapped around said junction of said lug nuts with said arms.

10. The maxillomandibular fixation apparatus of claim 9, wherein said fixation apparatus further comprises at least one exterior receiving bar having a similar arcuate shape as said interior arch bar, said at least one exterior receiving bar is alignable around the exterior or buccal surfaces either of the mandible teeth and maxilla teeth, said at least one exterior receiving bar having a plurality of holes therethrough for insertion of said distal ends of said arms;

wherein said at least one exterior receiving bar is securable to said arch bar interior of the teeth by insertion of the distal ends of each arm of said segments through said holes in said at least one exterior receiving bar, and connection of said lug nuts to said distal ends.

11. A maxillomandibular fixation apparatus for locking together the teeth of the upper and lower jaws, and/or for locking the upper and lower jaws together for a patient having a need therefor, the fixation apparatus comprising:

at least one arch bar positionable interior to the teeth either of the upper jaw and lower jaw; said arch bar adapted to be disposed adjacent to and extendable along the inside of teeth to be fixated;

a plurality of receptacle segments, each of said segments including:
  a base connectable to said arch bar adapted to be installed on the interior side of the teeth; and
  at least two arms extendable radially outward from each of said receptacle segments of said arch bar adapted to be installed interior of the teeth, said arms being positionable between teeth to be fixated, said arms having distal ends extendable outward on either side of each tooth towards the patient's cheeks;

an exterior receiving bar, said exterior receiving bar having a similar arcuate shape as said arch bar adapted to be installed interior of the teeth, said exterior receiving bar is adapted to be aligned around the exterior surfaces either of the mandible and maxilla teeth, said exterior receiving bar having a plurality of holes therethrough, said distal ends of said arms insertable through said plurality of holes; and a plurality of lug nuts, said lug nuts being connectable to said distal ends of each arm on the buccal side of said exterior receiving bar;

wherein said exterior receiving bar is securable to said arch bar installed interior of teeth to be fixated by connection of said lug nuts to each of said distal ends of said arms extended through said plurality of holes in said exterior receiving bar, for locking the teeth between said exterior receiving bar and said arch bar installed interior of the teeth.

12. The maxillomandibular fixation apparatus of claim 11, wherein said at least one arch bar is flexible and of metal composition, said at least one arch bar adapted to be installed interior of the teeth toward the tongue of the jaw, said at least one arch bar including a first arch bar installed interior of the teeth of the upper jaw and a second arch bar installed interior of the teeth of the lower jaw, said exterior receiving bar including a first exterior receiving bar aligned around the exterior surfaces of the teeth of the upper jaw and a second exterior receiving bar aligned around the teeth of the lower jaw.

13. The maxillomandibular fixation apparatus of claim 12, wherein said lug nuts are removably connectable to said distal ends, said lug nuts being in contact with the exterior, buccal interproximal side of the teeth when tightened toward said arch bar positioned on the lingual interior side of the teeth.

14. The maxillomandibular fixation apparatus of claim 13, wherein said receptacle segments are generally U-shaped, said distal ends having a hollow cylindrical cross-section and internally threaded, said distal ends accepting connection of said lug nuts, said base of each segment rigidly connected to said arch bar installed interior of the teeth.

15. The maxillomandibular fixation apparatus of claim 14, wherein said lug nuts comprise a first end having a blind bore therein, said blind bore having a hexagonal cross-section, and an insertion end having exterior threads for removable insertion into said distal ends of said arms of said receptacle segments.

16. The maxillomandibular fixation apparatus of claim 13, wherein said receptacle segments are generally U-shaped, said distal ends having external threads, said distal ends accepting connection of said lug nuts, said base of each segment rigidly connected to said arch bar installed interior of the teeth.

17. The maxillomandibular fixation apparatus of claim 16, wherein said lug nuts comprise a first end having a blind bore therein, said blind bore having a hexagonal cross-section, and a connection end having a cylindrical blind bore therein, said cylindrical blind bore having internal threads for removable connection to each distal end of said arms of said receptacle segments.

18. A method of fixating the teeth of a maxilla or mandibula of a patient having a need therefor, comprising the steps of:

(a) providing at least one unitary arcuate arch bar for connecting to the teeth;

(b) positioning said unitary arch bar on the interior of the teeth of either the upper jaw and lower jaw, said unitary arch bar being disposed parallel to the interior lingual side of the teeth, said unitary arch bar including a plurality of spaced apart arms projecting from said unitary arch bar, each of said arms being integrally formed to said arcuate arch bar, each of said arms extending radially outwardly beyond the teeth;

(c) inserting each of said arms between respective ones of the teeth, said arms having distal ends extending outwardly beyond the exterior, buccal interproximal side of the teeth; and (d) applying a locking means to each of said distal ends of said arms, thereby removably securing said unitary arch bar to the teeth.

19. The method of fixating the teeth of a maxilla or mandibula of claim 18, wherein said method further comprises the steps of:

(a) positioning a like configured unitary arch bar on the interior of the teeth of the jaw opposed from the positioning of said unitary arch bar, inserting each of said arms of said like configured unitary arch bar between the teeth, and attaching lug nuts onto each of said distal ends of said arms extending outwardly past the exterior, buccal interproximal side of the teeth of both of the upper jaw and lower jaw;

(b) tightening said lug nuts against the exterior, buccal interproximal side of the teeth of the upper jaw and lower jaw, thereby fixating said unitary arch bar and said like configured unitary arch bar to the respective teeth of the upper jaw and lower jaw; and (c) wrapping either of ligature wire and elastic bands between a selected number of said arms of said unitary arch bars extending outwardly between the teeth of the upper jaw and lower jaw; thereby locking said lug nuts and said arms of said unitary arch bars of the upper jaw and lower jaw together.

20. The method of fixating the teeth of a maxilla or mandibula of claim 19, wherein said method further comprises the steps of:

(a) positioning at least one exterior receiving bar having holes therethrough on the exterior of the teeth of the upper jaw, and on the exterior of the teeth of the lower jaw, each of said distal ends of said arms of said unitary arch bars extending outwardly between the teeth, and through said holes in each of said at least one exterior receiving bar;

(b) fixating said unitary arch bars and said at least one exterior receiving bar by attaching a lug nut to each of said distal ends of said arms extending outwardly between the teeth of the upper and lower jaws and through said holes in each of said at least one exterior receiving bar;

(c) locking the teeth by tightening said lug nut on each of said distal ends, thereby tightening said at least one exterior receiving bar against the exterior of the teeth of the upper jaw and lower jaw; and (d) wrapping either of ligature wire and elastic bands between a selected number of said arms of said unitary arch bars extending outwardly between the teeth of the upper jaw and lower jaw and trough said holes in each of said exterior receiving bar;

thereby locking together said lug nuts on said selected number of said arms of said unitary arch bars extending outward between the teeth of the upper jaw and lower jaw and through said holes in each of said exterior receiving bar for fixation of the upper jaw to the lower jaw.

\* \* \* \* \*